United States Patent
Blanc-Magnard et al.

(10) Patent No.: US 7,332,620 B2
(45) Date of Patent: Feb. 19, 2008

(54) PROCESS FOR THE PREPARATION OF SILICONE OILS CARRYING A GROUP COMPRISING AT LEAST ONE HYDROCARBON-COMPRISING RING IN WHICH IS INCLUDED AN OXYGEN ATOM

(75) Inventors: Delphine Blanc-Magnard, Lyons (FR); Sébastien Sterin, Lyons (FR)

(73) Assignee: Rhodia Chimie, Aubervilliers (FR)

( * ) Notice: Subject to any disclaimer, the term of this patent is extended or adjusted under 35 U.S.C. 154(b) by 572 days.

(21) Appl. No.: 10/493,844

(22) PCT Filed: Oct. 29, 2002

(86) PCT No.: PCT/FR02/03715

§ 371 (c)(1), (2), (4) Date: Nov. 19, 2004

(87) PCT Pub. No.: WO03/037961

PCT Pub. Date: May 8, 2003

(65) Prior Publication Data

US 2005/0107247 A1    May 19, 2005

(30) Foreign Application Priority Data

Oct. 30, 2001    (FR) ................................. 01 14039

(51) Int. Cl.
  *C07F 7/08* (2006.01)
  *C07F 7/02* (2006.01)
(52) U.S. Cl. ...................... 556/462; 556/450; 556/451; 556/453; 556/456

(58) Field of Classification Search ................. 556/450, 556/451, 462, 456, 453
See application file for complete search history.

(56) References Cited

U.S. PATENT DOCUMENTS 4,820,674 A * 4/1989 Shiozawa et al. ........... 502/169

FOREIGN PATENT DOCUMENTS

| EP | 0 277 023 | 8/1988 |
| EP | 0 545 591 | 6/1993 |
| EP | 0 578 354 | 1/1994 |
| FR | 2 749 850 | 12/1997 |
| FR | 2 750 349 | 1/1998 |
| FR | 2 813 081 | 2/2002 |

* cited by examiner

*Primary Examiner*—Elvis O. Price
(74) *Attorney, Agent, or Firm*—Buchanan, Ingersoll & Rooney, PC

(57) ABSTRACT

Process for the preparation of a functionalized silicone oil by hydrosilylation of synthons in the presence of at least one organohydrosilicon compound, characterized in that:
  (1) the synthons hydrosilylated with the organohydrosilicon compound are identical or different, and comprise at least one hydrocarbon-comprising ring in which is included at least one oxygen atom,
  (2) the said hydrosilylation reaction is carried out in the presence of a homogeneous catalytic system comprising (i) a metal, preferably a complexed metal, chosen from the group consisting of cobalt, rhodium, ruthenium, platinum and nickel and (ii) a heterocyclic organic compound chosen from lactones, lactams, cyclic carbonates and cyclic carbamates.

12 Claims, No Drawings

PROCESS FOR THE PREPARATION OF SILICONE OILS CARRYING A GROUP COMPRISING AT LEAST ONE HYDROCARBON-COMPRISING RING IN WHICH IS INCLUDED AN OXYGEN ATOM

The present invention relates to a novel process for the preparation of silicone oils modified by groups comprising at least one hydrocarbon-comprising ring in which is included at least one oxygen atom. More specifically, a subject-matter of the present invention is a process for hydrosilylation between organohydrosilicon compounds and synthons comprising at least one unsaturated functional group and at least one hydrocarbon-comprising ring in which is included an oxygen atom in which the gelling phenomenon resulting from the polymerization of the rings including an oxygen atom is inhibited.

Reactions between polyorganohydrosiloxanes and olefins or acetylenic hydrocarbons are very well-known. The polyorganohydrosiloxanes are, for example, of formulae: $Me_3SiO-(MeHSiO)_n-(Me_2SiO)_m-SiMe_3$, where $1 \leq n \leq 1000$ and $0 < m \leq 1000$, and $Me_2HSiO-(MeHSiO)_o-(Me_2SiO)_p-SiHMe_2$, where $0 < o \leq 1000$ and $0 < p \leq 1000$.

Numerous synthons can functionalize polyorganohydrosiloxanes; for example, alkenes, styrenes, allyl alcohols, allyloxy ethers or allylamines are used as synthons.

These reactions are very commonly used for the synthesis of functionalized silicone oils and the oils obtained have applications in highly varied fields, such as antiadhesion or lubrication. For example, functionalized silicone oils can be prepared with 1,2-epoxy-4-vinylcyclohexane synthons; the functionalized silicone oils obtained can subsequently be crosslinked thermally in the presence of an acidic catalyst (HCl, $H_2SO_4$) or photochemically in the presence, for example, of a cationic photoinitiator.

Numerous catalytic compositions are described in the literature for hydrosilylation reactions; they may in particular comprise metals, such as platinum, rhodium, cobalt or palladium. Specific examples of such catalytic compositions are platinum halides and rhodium halides, for example $H_2PtCl_6$, $PtCl_2$, $(RhCl_3 \cdot xH_2O)$, complexes of platinum with siloxanes having unsaturated groups, complexes of platinum with olefins and cationic complexes of platinum with nitrites as ligands. One of the most widely employed in industry is the Karstedt catalytic composition disclosed in particular in U.S. Pat. No. 3,775,452; this Karstedt composition is composed of platinum complexes, the platinum having a formal and true degree of oxidation of zero (0), with the formula:

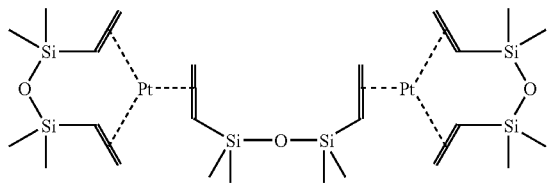

However, the conventional hydrosilylation processes of the prior art are not or not very suited to hydrosilylation reactions between polyorganohydrosiloxanes and synthons comprising a ring in which is included an oxygen atom (epoxide, and the like). The latter has a tendency to open and to cause uncontrolled polymerization and crosslinking reactions (gelling, formation of gum and/or of resin) of the functionalized oils which are initiated by the presence of the usual catalytic compositions, which also catalyse the polymerization of rings including an oxygen atom.

The Applicant Company has developed a novel process for the preparation of functionalized silicone oils by hydrosilylation which makes it possible to inhibit the opening of a ring including an oxygen atom present on the unsaturated synthon.

According to the hydrosilylation process of the present invention, the organohydrosilicon compound is reacted with different or identical synthons comprising a hydrocarbon-comprising ring in which is included at least one oxygen atom. This reaction is carried out in the presence of a homogeneous catalytic system comprising (i) at least one metal, preferably a completed metal, chosen from the group consisting of cobalt, rhodium, ruthenium, platinum, palladium and/or nickel and (ii) at least one heterocyclic organic compound chosen from lactones, lactams, cyclic carbonates and cyclic carbamates.

Preferably, the heterocyclic organic compounds comprise at least 5 atoms within the ring and are chosen from those of the formula below:

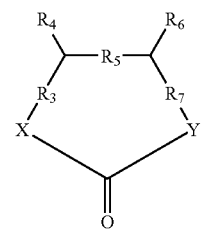

in which:
the X group represents O or $NR_8$,
the Y group represents O, $NR_9$ or a free valency,
the $R_3$, $R_5$ and $R_7$ groups, which are identical or different, represent (i) a free valency, (ii) a saturated or unsaturated and linear or branched alkyl radical which can be substituted, or (iii) a saturated or unsaturated and linear or branched alkylene radical which can be substituted,
the $R_4$ and $R_6$ groups, which are identical or different, represent (i) a hydrogen atom, (ii) a saturated or unsaturated and linear or branched alkyl radical which can be substituted, (iii) a saturated or unsaturated and linear or branched alkylene radical which can be substituted, or (iv) form a saturated or unsaturated hydrocarbon-comprising ring which can be substituted.

By way of examples, the heterocyclic compounds can be chosen from those of the formulae below:

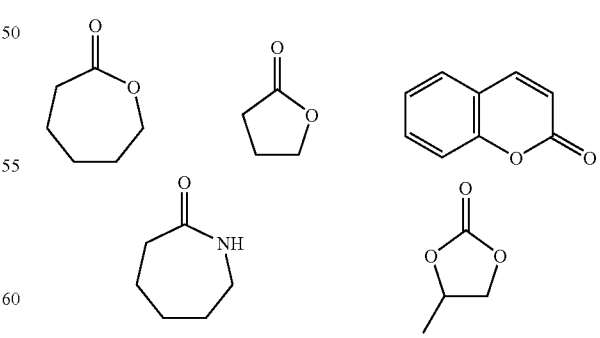

Other compounds are described in "*Synthesis of lactones and lactams*" by Michael A. Ogliaruso and James F. Wolfe [© 1993, John Wiley & Sons].

Preferably, the metal within the catalyst system is platinum, in particular with a degree of oxidation of zero.

Mention will in particular be made, as examples, of the complexed platinums of Karstedt type.

The organohydrosilicon compounds used in the process according to the invention are of two types: the silanes described below and the polyhydrosiloxanes described below.

The silanes correspond to the formula $Si(R_8)_{4-n}H$ with $1 \leq n \leq 3$ and $R_8$, which are identical or different, representing an alkyl radical, an aryl radical, an alkylaryl radical, an arylalkyl radical, a halogen (preferably chlorine), an alkoxy radical, an aryloxy radical, an alkylaryloxy radical or an arylalkyloxy radical.

The polyorganohydrosiloxanes used in the processes according to the invention are very diverse in nature. These polyorganohydrosiloxanes can be linear or cyclic and have the mean formulae:

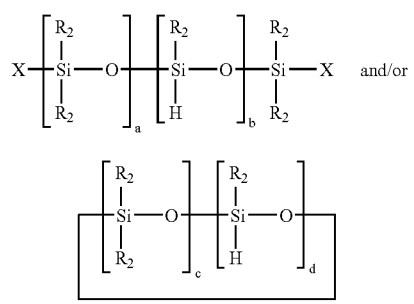

(XVI)

and/or (XVII)

in which:
the symbols $R_2$ are identical or different and correspond to a monovalent hydrocarbon-comprising radical chosen from the phenyl radical and linear or branched alkyl radicals having from 1 to 6 carbon atoms, preferably 1 to 3 carbon atoms;
the symbols X are identical or different and correspond to a monovalent radical chosen from $R_2$, a hydrogen atom, a methoxy radical and an ethoxy radical;
a and b are integers or fractions, such that:
  $0<a \leq 200$, preferably $0<a \leq 99$,
  $0 \leq b \leq 200$, preferably $1<b \leq 100$, and at least one of the two X groups corresponds to the hydrogen radical if b=0,
  $5<a+b \leq 200$, preferably $10<a+b \leq 100$;
c and d are integers or fractions, such that
  $0<c<5$, preferably $0<c<3$,
  $1<d<10$, preferably $1<d<5$,
  $3<c+d<10$, preferably $3<c+d<5$.

The synthons comprise at least one hydrocarbon-comprising ring in which is included an oxygen atom and have the formula:

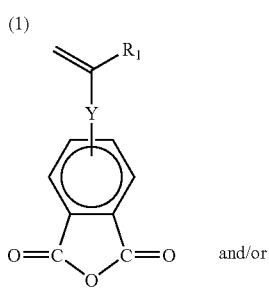

(III)

and/or

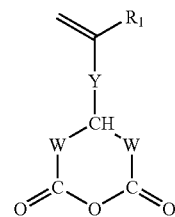

(IV)

in which:
the symbols W, which are identical or different, correspond to a divalent hydrocarbon-comprising radical chosen from linear or branched a kylene radicals having from 1 to 12 carbon atoms, it being possible for one of the symbols W to be a free valency;
the symbol Y corresponds to a free valency or a divalent radical chosen from linear or branched alkylene radicals having from 1 to 12 carbon atoms which can comprise a heteroatom, preferably an oxygen atom;
the symbol $R_1$ corresponds to a hydrogen atom or monovalent hydrocarbon-comprising radical chosen from linear or branched alkyl radicals having from 1 to 12 carbon atoms and preferably a hydrogen atom or a methyl radical;

(2)

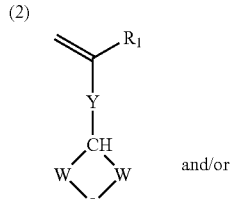

(V)

and/or

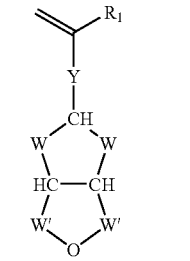

(VI)

in which:
the symbols W, which are identical or different, correspond to a divalent hydrocarbon-comprising radical chosen from linear or branched alkylene radicals having from 1 to 12 carbon atoms which can comprise at least one hydroxyl functional group, it being possible for one of the symbols W to be a free valency for (V) and it being possible for both symbols W simultaneously to be a free valency for (VI);
the symbols W', which are identical or different, correspond to a divalent hydrocarbon-comprising radical chosen from linear or branched alkylene radicals having from 1 to 12 carbon atoms, it being possible for at least one of the symbols W' to be a free valency;
the symbol Y corresponds to a free valency or a divalent radical chosen from linear or branched alkylene radicals having from 1 to 12 carbon atoms which can comprise a heteroatom, preferably an oxygen atom;

the symbol $R_1$ corresponds to a hydrogen atom or monovalent hydrocarbon-comprising radical chosen from linear or branched alkyl radicals having from 1 to 12 carbon atoms and preferably a hydrogen atom or a methyl radical; and (3)

(VII)

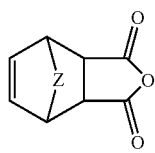

in which the symbol Z corresponds to a divalent radical chosen from a carbon atom or a heteroatom.

The hydrocarbon-comprising ring in which is included the oxygen atom preferably comprises at most 8 atoms in the said ring. Furthermore, the best results in agreement with the hydrosilylation process of the invention are obtained with synthons which only comprise one hydrocarbon-comprising ring in which is included an oxygen atom. In particular, the synthons used which give good results (see examples below) have the formula:

(VIII)

(IX)

(X)

(XI)

(XII)

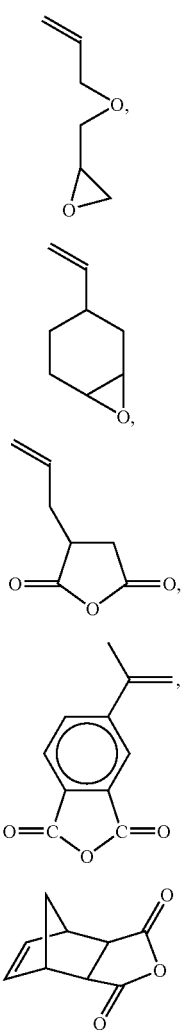

The synthons which react with the polyorganohydrosiloxane are generally identical synthons. The ratio of number of SiH units to the number of moles of sythons is between 0.01 and 100, preferably between 0.1 and 10.

The process according to the invention can be carried out according to various alternative forms. In particular, it is possible to use an implementation in which the combined reactants and catalytic system are mixed in the reaction mixture (batch type). The catalytic system can just as easily be prepared before use ("one pot" formulation) or prepared in the reaction mixture.

In the context of its experimental tests, the Applicant Company has developed an advantageous process in agreement with the first implementation. This process for hydrosilylation between a polyorganohydrosiloxane and an unsaturated synthon comprises the following stages:

(a) introduction into the reaction mixture of the catalytic system in which
  the metal content is from 5 to 5000 ppm, preferably from 10 to 100 ppm, with respect to the total mass of the reactants;
  and the molar ratio of the heterocyclic compound to the metal is between 10 and 10 000, preferably between 100 and 1000;
(b) introduction of the synthon into the reaction mixture;
(c) the said mixture is heated to a temperature of between 25° C. and 200° C. and preferably between 50° C. and 160° C.;
(d) the polyorganohydrosiloxane is subsequently introduced over a period of time of between 0 and 24 hours, preferably between 2.5 and 5 hours, the ratio of the number of SiH units to the number of moles of synthons being between 0.1 and 10.

According to a preferred form of this process, stage (b) is carried out before stage (a).

This advantageous process can be carried out in bulk, which means that the reaction between the polyorganohydrosiloxane and the synthon is carried out in the absence of solvent. However, numerous solvents, such as toluene, xylene, octamethyltetrasiloxane, cyclohexane or hexane, can be used. If appropriate, the functionalized silicone oil obtained is finally devolatilized.

The level of epoxy quantitatively determined in the oils obtained according to the invention is very high and the level of epoxy quantitatively determined/theoretical epoxy level ratio is between 0.95 and 1, this theoretical epoxy level corresponding to the level of ≡SiH quantitatively determined on the organohydrosilicon compound before reaction.

The silicone oils according to the invention, because of their properties, are thus employed as additive (for example, as diluent) or as main component in the formulation of crosslinkable compositions employed to prepare inks, varnishes and/or coatings; the coatings preferably being anti-adhesion coatings for paper, glass, plastic and/or metal.

These crosslinkable compositions generally comprise an initiator and an organic and/or silicone resin with epoxy and/or acrylate functionality; in addition, these compositions can comprise a diluent and/or a solvent. These compositions can be crosslinked, as the case may be, thermally, under U.V. radiation and/or under an electron beam.

EXAMPLES

The examples below demonstrate some of the advantages of the process for the preparation of functionalized silicone oils according to the present invention.

Examples 1 to 4 relate to the synthesis of epoxy-functionalized silicone oils obtained according to the process of the invention.

Examples 1' to 3' relate to the synthesis of epoxy-functionalized silicone oils according to modus operandi presented by way of comparison.

The platinum concentration is calculated with respect to the total mass of the alkene+SiH oil mixture.

The quantitative determination of the epoxide functional groups on the functionalized oils obtained is measured using a potentiometric device of 716 DMS Titrino type from Metrohm according to the method of I. M. Kolthoff and P. J. Elving ("Treatise on Analytical Chemistry", part II, vol. 14, p. 288).

Example 1

21.48 g (173 mmol) of 1,2-epoxy-4-vinylcyclo-hexane (hereinafter VCMX) and 21.5 mg (1000 ppm by weight of VCMX, i.e. 0.19 mmol) of ε-caprolactone are placed in a 100 ml reactor.

The reaction mixture is heated at 70° C. with stirring. 5.5 μl (10 ppm) of a solution of Karstedt catalyst comprising 10% of platinum are added to the reactor and 35 g (157.3 mmol) of heptamethylhydrotrisiloxane are subsequently run in dropwise over 3 hours onto the VCMX.

After reacting for 5 hours, the degree of conversion of the SiH units is 100%, and 1% of the epoxide functional groups have disappeared. The reaction is then halted.

The viscosity of the crude reaction mixture at 25° C. is measured: v=5.6 mPa·s.

Example 2

21.48 g (173 mmol) of VCMX and 21.5 mg (1000 ppm by weight of VCMX, i.e. 0.25 mmol) of γ-butyrolactone are placed in a 100 ml reactor. The reaction mixture is heated at 70° C. with stirring. 5.5 μl (10 ppm) of a solution of Karstedt catalyst comprising 10% of platinum are added to the reactor, and 35 g (157.3 mmol) of heptamethylhydrotrisiloxane are subsequently run in dropwise over 3 hours onto the VCMX.

After reacting for 5 hours, the degree of conversion of the SiH units is 100%, and 1.8% of the epoxide functional groups have disappeared. The reaction is then halted.

The viscosity of the crude reaction mixture at 25° C. is measured: v=6 mPa·s.

Example 3

21.48 g (173 mmol) of VCMX and 28 mg (1280 ppm by weight of VCMX, i.e. 0.187 mmol) of coumarin in solution (10% by weight/volume of toluene) are placed in a 100 ml reactor. The reaction mixture is heated at 70° C. with stirring. 5.5 μl (10 ppm) of a solution of Karstedt catalyst comprising 10% of platinum are added to the reactor, and 35 g (157.3 mmol) of heptamethylhydrotrisiloxane are subsequently run in dropwise over 3 hours onto the VCMX.

After reacting for 7 hours, the degree of conversion of the SiH units is greater than 99.9%, and 2% of the epoxide functional groups have disappeared. The reaction is then halted.

The viscosity of the crude reaction mixture at 25° C. is measured: v=6 mPa·s.

Example 4

21.48 g (173 mmol) of VCMX and 21.5 mg (1000 ppm by weight of VCMX, i.e. 0.190 mmol) of ε-caprolactam are placed in a 100 ml reactor. The reaction mixture is heated at 70° C. with stirring. 5.5 μl (10 ppm) of a solution of Karstedt catalyst comprising 10% of platinum are added to the reactor, and 35 g (157.3 mmol) of heptamethylhydrotrisiloxane are subsequently run in dropwise over 3 hours onto the VCMX.

After reacting for 7 hours, the degree of conversion of the SiH units is greater than 97.3%, and 2% of the epoxide functional groups have disappeared.

Example 1'

21.48 g (173 mmol) of VCMX are placed in a 100 ml reactor. The reaction mixture is heated at 70° C. with stirring. 5.5 μl (10 ppm) of a solution of Karstedt catalyst comprising 10% of platinum are added to the reactor, and 35 g (157.3 mmol) of heptamethylhydrotrisiloxane are subsequently run in dropwise over 3 hours onto the VCMX.

After reacting for 5 hours, the degree of conversion of the SiH units is 99% but 12% of the epoxide functional groups have disappeared. After reacting for 7 hours, the degree of conversion of the SiH units is 99.3%, and 23% of the epoxide functional groups have disappeared. The reaction is then halted.

The viscosity of the crude reaction mixture at 25° C. is measured: v=38 mPa·s. This value is six times higher than that of Example 1; this demonstrates that a portion of the epoxide functional groups present in the medium have polymerized during the hydrosilylation reaction in the presence of the Karstedt catalyst alone.

Example 2'

21.48 g (173 mmol) of VCMX and 18.5 mg (860 ppm by weight of VCMX, i.e. 0.189 mmol) of cyclohexanone are placed in a 100 ml reactor. The reaction mixture is heated at 70° C. with stirring. 5.5 μl (10 ppm) of a solution of Karstedt catalyst comprising 10% of platinum are added to the reactor, and 35 g (157.3 mmol) of heptamethylhydrotrisiloxane are subsequently run in dropwise over 3 hours onto the VCMX.

After reacting for 3 hours, the degree of conversion of the SiH units is 93.8%, and 4.4% of the epoxide functional groups have disappeared. After reacting for 5 hours, the degree of conversion of the SiH units is 98.4%, and 9.9% of the epoxide functional groups have disappeared. After reacting for 7 hours, the degree of conversion of the SiH units is 98.8%, and 19.5% of the epoxide functional groups have disappeared.

The reaction is then halted. The viscosity of the crude reaction mixture at 25° C. is measured: v=28 mPa·s. This example shows that the cyclohexanone does not make it possible to avoid the polymerization of a portion of the epoxide functional groups during the reaction.

Example 3'

21.48 g (173 mmol) of VCMX and 24.5 mg (1140 ppm by weight of VCMX, i.e. 0.188 mmol) of methyl caproate are are placed in a 100 ml reactor. The reaction mixture is heated at 70° C. with stirring. 5.5 μl (10 ppm) of a solution of Karstedt catalyst comprising 10% of platinum are added to the reactor, and 35 g (157.3 mmol) of heptamethylhydrotrisiloxane are subsequently run in dropwise over 3 hours onto the VCMX.

After reacting for 3 hours, the degree of conversion of the SiH units is 92%, and 2% of the epoxide functional groups have disappeared. After reacting for 5 hours, the degree of conversion of the SiH units is 99.2%, and 4.7% of the epoxide functional groups have disappeared. After reacting for 7 hours, the degree of conversion of the SiH units is 99.4% but 8% of the epoxide functional groups have disappeared. The reaction is then halted.

The viscosity of the crude reaction mixture at 25° C. is measured: v=8.4 mPa·s. This experiment shows that the methyl caproate does not make it possible to prevent a portion of the epoxide functional groups present in the medium from polymerizing during the reaction.

The invention claimed is:
1. Process for the preparation of a functionalized silicone oil by hydrosilylation of synthons in the presence of at least one organohydrosilicon compound, wherein:
   (1) the synthons hydrosilylated with the organohydrosilicon compound are identical or different, and comprise at least one hydrocarbon-comprising ring in which is included at least one oxygen atom,
   (2) the said hydrosilylation reaction is carried out in the presence of a homogeneous catalytic system comprising (i) a metal selected from the group consisting of cobalt, rhodium, ruthenium, platinum and nickel and (ii) a heterocyclic organic compound chosen from lactones, lactams, cyclic carbonates and cyclic carbamates.

2. Process according to claim 1, wherein the organohydrosilicon compound is a linear or cyclic polyorganohydrosiloxane of mean formulae:

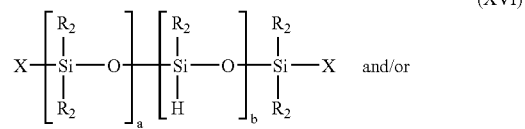
(XVI)

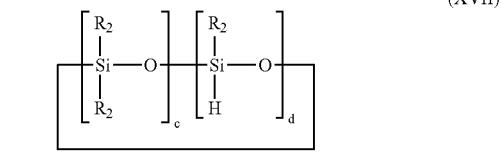
(XVII)

in which:
   the symbols $R_2$ are identical or different and correspond to a monovalent hydrocarbon-comprising radical selected from the phenyl radical and linear or branched alkyl radicals having from 1 to 6 carbon atoms;
   the symbols X are identical or different and correspond to a monovalent radical chosen from $R_2$, a hydrogen atom, a methoxy radical and an ethoxy radical;
   a and b are integers or fractions, wherein:
      $0<a\leq200$,
      $0\leq b\leq200$,
      and at least one of the two X groups corresponds to the hydrogen radical if b=0,
      $5<a+b\leq200$;
   c and d are integers or fractions, such that:
      $0<c<5$,
      $1<d<10$,
      $3<a+<10$.

3. Process according to claim 1, wherein the organohydrosilicon compound is a silane of formula $Si(R_8)_{4-n}H$ with $1\leq n\leq3$ and $R_8$, which are identical or different, representing an alkyl radical, an aryl radical, an alkylaryl radical, an arylalkyl radical, a halogen, an alkoxy radical, an aryloxy radical, an alkylaryloxy radical or an arylalkyloxy radical.

4. Process according to claim 1, wherein the heterocyclic organic compound comprises at least 5 atoms within the ring and is selected from those of the formula below:

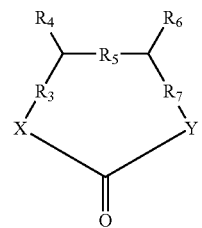

in which:
   the X group represents O or $NR_8$,
   the Y group represents O, $NR_9$ or a free valency,
   the $R_3$, $R_5$ and $R_7$ groups, which are identical or different, represent (i) a free valency, (ii) a saturated or unsaturated and linear or branched alkyl radical which can be substituted, or (iii) a saturated or unsaturated and linear or branched alkylene radical which can be substituted,
   the $R_4$ and $R_6$ groups, which are identical or different, represent (i) a hydrogen atom, (ii) a saturated or unsaturated and linear or branched alkyl radical which can be substituted, (iii) a saturated or unsaturated and linear or branched alkylene radical which can be substituted, or (iv) form a saturated or unsaturated hydrocarbon-comprising ring which can be substituted.

5. Process according to claim 1, wherein the metal of the catalytic system is platinum.

6. Process according to claim 1, wherein the amount of metal in the catalytic system is between 1 and 1000 ppm with respect to the weight of the organohydrosilicon compound.

7. Process according to claim 1, wherein the synthons comprise at least one hydrocarbon-comprising ring in which is included an oxygen atom, the synthons having the formula:

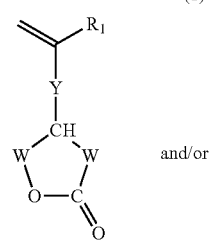
(I)

and/or

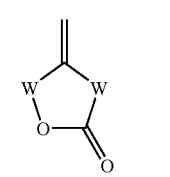
(II)

in which:
   the symbols W are identical or different and correspond to a divalent hydrocarbon-comprising radical selected from linear or branched alkylene radicals having from 1 to 12 carbon atoms, it being possible for one of the symbols W to be a free valency;

the symbol Y corresponds to a free valency or a divalent radical selected from linear or branched alkylene radicals having from 1 to 12 carbon atoms which can comprise a heteroatom;

the symbol $R_1$ corresponds to a hydrogen atom or monovalent hydrocarbon-comprising radical selected from linear or branched alkyl radicals having from 1 to 12 carbon atoms;

(2)

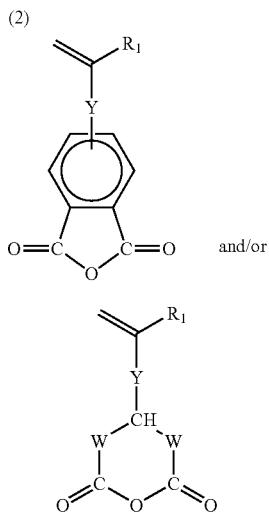

and/or in which:

the symbols W are identical or different and correspond to a divalent hydrocarbon-comprising radical selected from linear or branched alkylene radicals having from 1 to 12 carbon atoms, it being possible for one of the symbols W to be a free valency;

the symbol Y corresponds to a free valency or a divalent radical selected from linear or branched alkylene radicals having from 1 to 12 carbon atoms which can comprise a heteroatom;

the symbol $R_1$ corresponds to a hydrogen atom or monovalent hydrocarbon-comprising comprising radical selected from linear or branched alkyl radicals having from 1 to 12 carbon atoms; and (3)

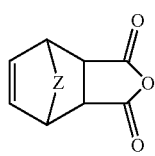

(VII)

in which:

the symbol Z corresponds to a divalent radical selected from a carbon atom or a heteroatom.

8. Process according to claim 7, wherein the hydrocarbon-comprising ring of the synthons comprises at most 8 atoms in the said ring.

9. Process according to claim 7, wherein the synthon has the formula:

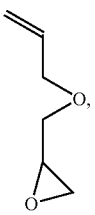

(VIII)

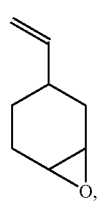

(IX)

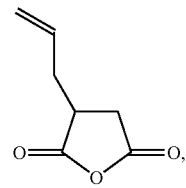

(X)

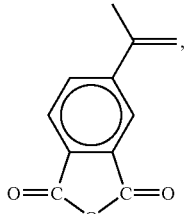

(XI)

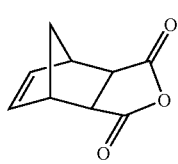

(XII)

10. Process according to claim 1, wherein the synthons which react with the organohydrosilicon compound are identical synthons.

11. Process according to claim 1, wherein the organohydrosilicon compound/synthons molar ratio is between 0.01 and 100.

12. Process according to claim 1, wherein the organohydrosilicon compound and the synthon react in the reaction mixture in the absence of solvent.

* * * * *